(12) United States Patent
Peltier et al.

(10) Patent No.: US 12,011,474 B2
(45) Date of Patent: *Jun. 18, 2024

(54) COMPOSITION COMPRISING A MIXTURE OF MOLECULES EXTRACTED FROM CHRYSANTHELLUM INDICUM, CYNARA SCOLYMUS AND LYCIUM BARBARUM AND USE TO ACT ON CARBOHYDRATE AND/OR FAT METABOLISM

(71) Applicants: VALBIOTIS, Perigny (FR); Universite Clermont Auvergne, Clermont-Ferrand (FR)

(72) Inventors: Sebastien Peltier, Fouras (FR); Vivien Chavanelle, Clermont-Ferrand (FR); Pascal Sirvent, Ceyrat (FR)

(73) Assignees: VALBIOTIS, Perigny (FR); UNIVERSITE CLERMONT AUVERGNE, Clermont-Ferrand (FR)

( * ) Notice: Subject to any disclaimer, the term of this patent is extended or adjusted under 35 U.S.C. 154(b) by 350 days.

This patent is subject to a terminal disclaimer.

(21) Appl. No.: 16/990,290

(22) Filed: Aug. 11, 2020

(65) Prior Publication Data

US 2020/0368303 A1 Nov. 26, 2020

Related U.S. Application Data

(63) Continuation of application No. 15/769,876, filed as application No. PCT/EP2016/075257 on Oct. 20, 2016, now Pat. No. 10,813,965.

(30) Foreign Application Priority Data

Oct. 20, 2015 (FR) ........................... 1559965

(51) Int. Cl.

| A61K 36/287 | (2006.01) |
| A23L 33/105 | (2016.01) |
| A61K 9/00 | (2006.01) |
| A61K 9/20 | (2006.01) |
| A61K 9/48 | (2006.01) |
| A61K 31/197 | (2006.01) |
| A61K 31/4188 | (2006.01) |
| A61K 31/4525 | (2006.01) |
| A61K 31/455 | (2006.01) |
| A61K 31/51 | (2006.01) |
| A61K 31/519 | (2006.01) |
| A61K 31/525 | (2006.01) |
| A61K 31/593 | (2006.01) |
| A61K 31/675 | (2006.01) |
| A61K 31/714 | (2006.01) |
| A61K 33/24 | (2019.01) |
| A61K 33/30 | (2006.01) |
| A61K 35/747 | (2015.01) |
| A61K 36/28 | (2006.01) |
| A61K 36/45 | (2006.01) |
| A61K 36/63 | (2006.01) |
| A61K 36/67 | (2006.01) |
| A61K 36/815 | (2006.01) |
| A61K 45/06 | (2006.01) |
| A61P 3/06 | (2006.01) |

(Continued)

(52) U.S. Cl.
CPC .......... *A61K 36/287* (2013.01); *A23L 33/105* (2016.08); *A61K 9/0095* (2013.01); *A61K 9/2009* (2013.01); *A61K 9/2054* (2013.01); *A61K 9/4825* (2013.01); *A61K 9/485* (2013.01); *A61K 9/4858* (2013.01); *A61K 9/4866* (2013.01); *A61K 31/197* (2013.01); *A61K 31/4188* (2013.01); *A61K 31/4525* (2013.01); *A61K 31/455* (2013.01); *A61K 31/51* (2013.01); *A61K 31/519* (2013.01); *A61K 31/525* (2013.01); *A61K 31/593* (2013.01); *A61K 31/675* (2013.01); *A61K 31/714* (2013.01); *A61K 33/24* (2013.01); *A61K 33/30* (2013.01); *A61K 35/747* (2013.01); *A61K 36/28* (2013.01); *A61K 36/45* (2013.01); *A61K 36/63* (2013.01); *A61K 36/67* (2013.01); *A61K 36/815* (2013.01); *A61K 45/06* (2013.01); *A61P 3/06* (2018.01); *A61P 3/10* (2018.01); *A23V 2002/00* (2013.01); *A61K 9/48* (2013.01); *A61K 2035/115* (2013.01); *A61K 2236/15* (2013.01); *A61K 2236/333* (2013.01); *A61K 2236/51* (2013.01)

(58) Field of Classification Search
None
See application file for complete search history.

(56) References Cited

U.S. PATENT DOCUMENTS

2007/0009620 A1 1/2007 Aoki et al.
2011/0288125 A1 11/2011 Park

FOREIGN PATENT DOCUMENTS

| CN | 101757271 | * | 6/2010 |
| CN | 104383116 A | | 3/2015 |
| FR | 2827774 | * | 1/2003 |

(Continued)

OTHER PUBLICATIONS

Meghwal et al., Phytotheraphy Research, 27, 1121-1130-2013.*

*Primary Examiner* — Michael V Meller
(74) *Attorney, Agent, or Firm* — Greer, Burns & Crain, Ltd.

(57) ABSTRACT

A composition comprising at least a mixture of molecules extracted from *Chrysanthellum indicum*, *Cynara scolymus* and *Lycium barbarum*. This composition is in particular useful as a nutritional product or health product to prevent and/or combat fat and/or carbohydrate metabolism disorders in Humans or animals.

8 Claims, 2 Drawing Sheets

(51) Int. Cl.
*A61P 3/10* (2006.01)
*A61K 35/00* (2006.01)

(56) References Cited

FOREIGN PATENT DOCUMENTS

| WO | WO2013037857 A1 | 3/2013 |
| WO | WO2016062958 A1 | 4/2016 |

* cited by examiner

Mean values ± ESM; Control, n = 10; C4, n = 10. Unpaired t test.

COMPOSITION COMPRISING A MIXTURE OF MOLECULES EXTRACTED FROM CHRYSANTHELLUM INDICUM, CYNARA SCOLYMUS AND LYCIUM BARBARUM AND USE TO ACT ON CARBOHYDRATE AND/OR FAT METABOLISM

CROSS-REFERENCE TO RELATED APPLICATIONS

This application is a continuation application of U.S. application Ser. No. 15/769,876, filed Apr. 20, 2018, which is a US national stage application of PCT/EP2016/075257, filed Oct. 20, 2016, which claims a benefit of priority from French patent application FR 1559965, filed Oct. 20, 2015, the entire disclosures of which are incorporated herein by reference.

TECHNICAL FIELD

The present invention relates to the prevention and treatment of fat and/or carbohydrate metabolism disorders in Humans or animals.

BACKGROUND

The serous concentrations of whole cholesterol and LDL cholesterol are above recommended values in many people within developed countries and in urbanized regions. This is partially due to poor lifestyle habits, in particular dietary habits. However, epidemiological studies have clearly demonstrated that an elevation in the plasma concentration of LDL cholesterol increases the risk of cardiovascular disease. Reducing plasma LDL cholesterol levels (whether through dietary change or the use of therapeutic agents) generally causes a decrease in cardiovascular events, in both primary prevention and secondary prevention (Wilson P W et al. Am J Cardiol 1987; 59:91G-94G). In recent meta-analyses, it has been calculated that cardiovascular risk dropped by 20% for each reduction of 1 mmol/L of LDL cholesterol, irrespective of the therapeutic molecule used (Robison J G et al. J Am Coll Cardiol 2005; 46:1855-1862; Baigent C et al. Lancet 2005; 366:1267-78).

The data obtained in different countries shows that the first therapeutic objective is to establish a correspondence between the intensity of the drop in LDL cholesterol and the absolute risk of cardiovascular disease. First of all, anyone with elevated LDL cholesterol should make lifestyle changes; in compliant individuals, this first strategy is generally effective. Secondly, subjects at high risk for cardiovascular disease should also be placed on medicinal treatment. The main lipopenic drugs are:

Statins: simvastatin name brand and generic, pravastatin name brand and generic, fluvastatin name brand and generic, atorvastatin and rosuvastatin;
Statins associated with fixed doses: simvastatin+ezetimibe, pravastatin+acetylsalicilic acid, atorvastatin+amlodipine;
Fibrates: fenofibrate name brand and generic, bezafibrate, gemfibrozil, cipofibrate name brand and generic;
Nicotinic acid;
Ion exchange resins: cholestyramine;
Cholesterol absorption inhibitors: ezetimibe;
Omega-3 polyunsaturated fatty acids;
Others: tiadenol.

These hypolipidemic drugs are effective on the cardiovascular level, but they are costly and above all have major side effects, causing decreased compliance, or even a complete cessation of use by patients.

The statins available at this time may cause, inter alia, myopathies with symptoms such as myalgia, fatigue and muscle stiffness and cramps, paradoxically causing patients to reduce their physical activity level. Furthermore, the risk of myopathies is exacerbated with the simultaneous administration of statins and fibrates (Denke M A J Manag Care Pharm 2003; 9:17-9).

Thus, in the context of patients having both an increased cholesterolemia and triglyceridemia, the statins+fibrates association may prove dangerous. However, it is essential to decrease the blood triglyceride level, since a high level increases the risk of atherosclerosis (Brinton E A Cardiol Clin 2015; 33:309-323). Statins may also increase the risk of other pathologies, such as breast cancer (from Lorgeril M et al. BMC Med 2014; 12:94).

Furthermore, insulin resistance is one of the most important mechanisms of the development of many pathologies, including metabolic syndrome and atherosclerosis (Samuel V T et al. Cell 2012; 148:852-71+Kim B et al. Exp Mol Med 2015; 47(3):e149).

There is therefore a real need for products able to be used both during the silent establishment of cardio-metabolic pathologies, characterized by an elevation in certain risk factors (lipid abnormalities, carbohydrate abnormalities, excess weight, inflammation, oxidative stress, arterial hypertension), and upon the triggering of these pathologies, atherosclerosis and type 2 diabetes in particular.

There is also an urgent need for products able to be used as preventive solutions and medicaments, having a "multi-target" action mechanism with advantages in terms of compliance, tolerance and efficacy. Such products would make it possible to decrease the overall risk of cardio-metabolic disease and to prevent and treat each malfunction and/or its consequences considered independently.

SUMMARY

The aim of the invention is to meet these different needs by proposing compositions capable of acting simultaneously on several lipid malfunctions, the fasting blood glucose and insulin sensitivity, and that thus represent both a means of prevention and an advantageous therapeutic means to prevent and treat cardio-metabolic diseases and their complications. To satisfy its aim, the invention relates to compositions comprising at least a mixture of molecules extracted from *Chrysanthellum indicum*, *Cynara scolymus* and *Lycium barbarum*. Preferably, the composition according to the invention also comprises piperine.

Extracts of *Chrysanthellum indicum* and extracts of *Cynara scolymus* have already been described and some have been used in nutritional products, but unexpectedly, the combination of *Chrysanthellum indicum* with *Cynara scolymus* and *Lycium barbarum* leads to surprising results both on fat metabolism and carbohydrate metabolism in Humans or animals, these plants acting synergistically.

Advantageously, the compositions according to the invention act on dyslipidemia (cholesterol and triglycerides), but also on other cardiovascular risk factors such as excess weight and obesity, and blood pressure. They also prevent the establishment of chronic hyperglycemia and decrease the fasting blood glucose chronically, decrease the glycated hemoglobin, make it possible to improve the tolerance for the ingested carbohydrates and improve insulin sensitivity.

Furthermore, they have few or no side effects in light of those observed with the existing treatments and treatments in development.

The invention therefore also relates to the use of compositions as nutritional products or health products, in particular as medicaments, in particular to prevent and/or combat fat and/or carbohydrate metabolism disorders in Humans or animals.

The invention will now be described in detail in light of the appended figures, which show:

DEFINITIONS

Figure 1:
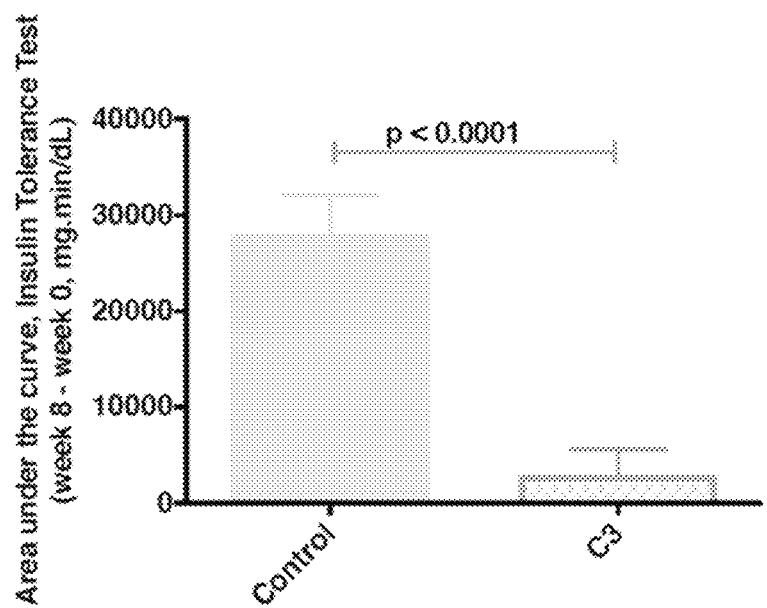
FIG. 1: the results for the effect of a composition comprising molecules extracted from *Chrysanthellum indicum* and *Cynara scolymus* on insulin sensitivity.

"Extract of plant "X" or plant raw material "X" refers, within the meaning of the invention, to a set of molecules obtained from plant "X" using any suitable method. One may in particular cite aqueous extracts (obtained using an aqueous solvent), alcoholic extracts (obtained using an alcoholic solvent) or using an organic solvent, or using a natural fat or mixture of natural fats, in particular a plant oil or a mixture of plant oils. An aqueous solvent refers to any solvent made up in whole or in part of water. Examples then include water itself, hydro-alcoholic solvents in any proportion or solvents made up of water and a compound such as glycerin or glycol propylene in any proportion. The alcoholic solvents in particular include ethanol. "Unique extract obtained from several plants "X" or plant raw materials "X"" refers, within the meaning of the invention, to a set of molecules obtained from a mixture of at least two plants "X" using any suitable method. One may in particular cite aqueous extracts (obtained using an aqueous solvent), alcoholic extracts (obtained using an alcoholic solvent) or using an organic solvent, or using a natural fat or mixture of natural fats, in particular a plant oil or a mixture of plant oils. An aqueous solvent refers to any solvent made up in whole or in part of water. Examples then include water itself, hydro-alcoholic solvents in any proportion or solvents made up of water and a compound such as glycerin or glycol propylene in any proportion. Alcoholic solvents in particular include ethanol.

"Mixture of extracts" refers, within the meaning of the invention, to the association of at least three extracts in solid, liquid or gaseous form that may or may not interact chemically. The mixture of extracts according to the invention is obtained using any method known by those skilled in the art. It may be obtained by simple mixing of the extracts.

"Plant" or "plant raw material" refers, within the meaning of the invention, to the whole plant or plant part, including the cell cultures, not yet having undergone a specific treatment and intended to be included in the manufacture of a plant preparation.

"Plant "X" not present in the unique extract" means, within the meaning of the invention, that the plant "X" has not been used to obtain the unique extract and that the unique extract does not comprise molecules extracted from this plant "X".

DETAILED DESCRIPTION OF THE INVENTION

In the present application, the singular or plural will be used indifferently to designate the compositions according to the invention.

The invention relates to a composition comprising at least a mixture of molecules extracted from *Chrysanthellum indicum*, *Cynara scolymus* and *Lycium barbarum*.

The molecules extracted from *Chrysanthellum indicum*, *Cynara scolymus* and *Lycium barbarum* act synergistically on the fat and carbohydrate metabolism.

In particular, the composition according to the invention comprises:
  a mixture made up of at least an extract of *Chrysanthellum indicum*, an extract of *Cynara scolymus* and an extract of *Lycium barbarum*, and/or
  a unique extract obtained from at least *Chrysanthellum indicum*, *Cynara scolymus* and *Lycium barbarum*, and/or
  a unique extract obtained from at least two plants, two of which will be chosen from among *Chrysanthellum indicum*, *Cynara scolymus* and *Lycium barbarum*, and at least one extract from a plant chosen from among *Chrysanthellum indicum*, *Cynara scolymus* et *Lycium barbarum* not present in the unique extract, and/or
  a unique extract obtained from at least two plants, one of which will be chosen from among *Chrysanthellum indicum*, *Cynara scolymus* and *Lycium barbarum*, and at least two extracts from plants chosen from among *Chrysanthellum indicum*, *Cynara scolymus* and *Lycium barbarum* not present in the unique extract.

The composition may also optionally contain piperine, an extract of *Olea europeae* and/or an extract of *Vaccinium myrtillus*.

According to a first embodiment, the composition according to the invention comprises at least one mixture of extracts made up of at least:
  an extract of *Chrysanthellum indicum*, and
  an extract of *Cynara scolymus*, and
  an extract of *Lycium barbarum*.

These three extracts act synergistically on the fat and carbohydrate metabolism.

Preferably, the composition according to the invention comprises piperine, either in the form of Piper extract or in the form of synthetic piperine.

The plant extracts can be obtained using any suitable method, for example through a method comprising the following steps:
  solid/liquid extraction
  separation/pressing
  filtration
  evaporation
  drying
  optionally, incorporating additives
  homogenization
  packaging.

The extract of *Chrysanthellum indicum* is preferably an extract from the whole plant or exposed parts.

It may in particular involve an extract that is hydroalcoholic or aqueous or subcritical $CO_2$ or subcritical $H_2O$ or associated with a heat treatment done by traditional heating or by microwave frequency or by ultrasound.

The plant/extract ratio is preferably comprised between 1/1 to 100/1, in particular between 1/1 and 25/1.

The composition according to the invention, when it is intended for Humans, preferably comprises a quantity of *Chrysanthellum indicum* extract allowing the administration of at least 0.00001 g, in particular between 0.00001 g and 0.60 g, of *Chrysanthellum indicum* extract per kg of body weight of the person to whom the composition is administered and per day.

Preferably, the *Chrysanthellum indicum* extract comprises molecules chosen from among apigenin-7-O-glucuronide, chrysanthellin A, chrysanthellin B, caffeic acid, luteolin, maritimetin, eriodictyol, isookanin, apigenin, luteolin-7-O-glucoside, maritimein, marein, eriodictyol-7-O-glucoside, flavomarein, apigenin-8-C-α-L-arabinoside-6-C-β-D-glucoside (shaftoside), apigenin-6,8-C-di-β-D-glucopyranoside (vicenin-2), or their analogues.

Within the meaning of the present invention, analogue refers to all compounds having a chemical structure similar to another compound, but different therefrom by a certain component. It may differ by one or several atoms, functional groups, substructures, which are replaced by other atoms, functional groups or substructures. Examples include apigenin-7-O-glucuronide such as apigenin-7-apioglucoside, apigenin-8-C-glucoside (vitexin), apigenin-6-C-glucoside (isovitexin), apigenin-7-O-neohesperidoside, apigenin-7-glucoside, apigenin-7-apioglucoside.

The extract of *Cynara scolymus* is preferably an extract from leaves or roots.

It may in particular involve an extract that is hydroalcoholic or aqueous or subcritical $CO_2$ or subcritical $H_2O$ or associated with a heat treatment done by traditional heating or by microwave frequency or by ultrasound.

The plant/extract ratio is preferably comprised between 1/1 to 100/1, in particular between 1/1 and 30/1.

The composition according to the invention, when it is intended for Humans, preferably comprises a quantity of *Cynara scolymus* extract allowing the administration of at least 0.00001 g, in particular between 0.00001 g and 0.60 g, of *Cynara scolymus* extract per kg of body weight of the person to whom the composition is administered and per day.

Preferably, the extract of *Cynara scolymus* comprises molecules chosen from among a dicafeoylquinic acid, a sulfo-monocafeoylquinic acid, luteolin, luteolin-7-O-glucoside, luteolin-7-O-glucuronide, apigenin-7-O-glucoside, cynaropicrin, or analogues thereof.

The extract of *Lycium barbarum* is preferably an extract from berries or exposed parts. It may in particular involve an extract that is hydroalcoholic or aqueous or subcritical $CO_2$ or subcritical $H_2O$ or associated with a heat treatment done by traditional heating or by microwave frequency or by ultrasound.

The plant/extract ratio is preferably comprised between 1/1 to 150/1, in particular between 1/1 and 90/1.

The composition according to the invention, when it is intended for Humans, preferably comprises a quantity of *Lycium barbarum* extract allowing the administration of at least 0.00001 g, in particular between 0.00001 g and 0.60 g, of *Lycium barbarum* extract per kg of body weight of the person to whom the composition is administered and per day.

Preferably, the extract of *Lycium barbarum* comprises at least polysaccharides such as xylose, mannose, arabinose or galactose.

In addition to the extract of *Chrysanthellum indicum*, *Cynara scolymus* and *Lycium barbarum*, the mixture according to the invention may also contain other compounds, in particular piperine and/or an extract of *Olea europaea*.

The piperine present in the composition according to the invention may be contained in an extract of Piper or may be a synthetic piperine.

The topological formula of the piperine is as follows:

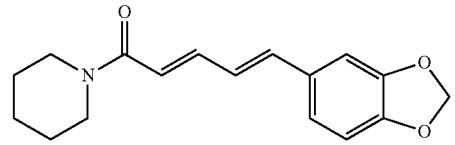 [SMILES: O=C(/C=C/C=C/c1ccc2c(c1)OCO2)N1CCCCC1]

The composition according to the invention, when it is intended for Humans, preferably comprises a quantity of piperine extract allowing the administration of at least 0.001 mg, in particular between 0.001 mg and 166 mg, of piperine extract per kg of body weight of the person to whom the composition is administered and per day.

If the piperine is contained in a *Piper* extract, the mixture of the composition according to the invention comprises said extract. The *Piper* extract is preferably an extract of *Piper nigrum*, *Piper aduncum* and/or *Piper* longum.

The *Piper* extract is preferably an extract from fruits or leaves.

It may in particular involve an extract that is hydroalcoholic or aqueous or subcritical $CO_2$ or subcritical $H_2O$ or associated with a heat treatment done by traditional heating or by microwave frequency or by ultrasound.

The plant/extract ratio is preferably comprised between 1/1 to 10000/1, in particular between 1/1 and 200/1.

The extract preferably comprises at least 1 wt % of piperine relative to the total weight of the extract.

The *Olea europaea* extract is preferably an extract from leaves or fruits.

It may in particular involve an extract that is hydroalcoholic or aqueous or subcritical $CO_2$ or subcritical $H_2O$ or associated with a heat treatment done by traditional heating or by microwave frequency or by ultrasound.

The plant/extract ratio is preferably comprised between 1/1 to 200/1, in particular between 1/1 and 60/1.

The composition according to the invention, when it is intended for Humans, preferably comprises a quantity of *Olea europaea* extract allowing the administration of at least 0.00001 g, in particular between 0.00001 g and 0.60 g, of *Olea europaea* extract per kg of body weight of the person to whom the composition is administered and per day.

Preferably, the extract of *Olea europaea* comprises at least one oleuropein and/or hydroxytyrosol and/or their analogues.

Preferably, the *Chrysanthellum indicum* extract/*Cynara scolymus* extract/*Lycium barbarum* extract ratio in the mixture of extracts is comprised between 0.001/0.001/0.001 and 10/10/10.

When the composition also comprises an extract of *Piper* or piperine, the *Chrysanthellum indicum* extract/*Cynara*

*scolymus* extract/*Lycium barbarum* extract ratio in the mixture is preferably comprised between 0.001/0.001/0.001/0.001 and 10/10/10/10.

When the composition comprises an extract of *Chrysanthellum indicum*, an extract of *Cynara scolymus*, a *Lycium barbarum* extract and an *Olea europaea* extract, the *Chrysanthellum indicum* extract/*Cynara scolymus* extract/*Lycium barbarum* extract/*Olea europaea* extract ratio in the mixture is preferably comprised between 0.001/0.001/0.001/0.001 and 10/10/10/10.

According to one alternative, in addition to the mixture made up of several plant extracts or in place of the mixture made up of several plant extracts, the composition according to the invention may comprise at least one unique extract.

The unique extract may be obtained from:
at least *Chrysanthellum indicum*, *Cynara scolymus* and *Lycium barbarum*,
at least two plants, two of which will be chosen from among *Chrysanthellum indicum*, *Cynara scolymus* and *Lycium barbarum*, and if the composition also comprises at least one extract from a plant chosen from among *Chrysanthellum indicum*, *Cynara scolymus* and *Lycium barbarum* not present in the unique extract; it may in particular involve:
  a composition comprising at least one unique extract obtained from at least *Chrysanthellum indicum* and *Cynara scolymus* and an extract of *Lycium barbarum*,
  a composition comprising at least one unique extract obtained from at least *Chrysanthellum indicum* and *Lycium barbarum* and an extract of *Cynara scolymus*,
  a composition comprising at least one unique extract obtained from at least *Lycium barbarum* and *Cynara scolymus* and an extract of *Chrysanthellum indicum*,
at least two plants, one of which is chosen from among *Chrysanthellum indicum*, *Cynara scolymus* and *Lycium barbarum*, and if the composition also comprises at least two plant extracts chosen from among *Chrysanthellum indicum*, *Cynara scolymus* and *Lycium barbarum* not present in the unique extract; it may in particular involve:
  a composition comprising at least one unique extract obtained from at least *Chrysanthellum indicum* and at least one other plant, for example *Piper* and/or *Olea* europeae, and an extract of *Cynara scolymus* and an extract of *Lycium barbarum*,
  a composition comprising at least one unique extract obtained from at least *Cynara scolymus* and at least one other plant, for example *Piper* and/or *Olea* europeae, and an extract of *Chrysanthellum indicum* and an extract of *Lycium barbarum*,
  a composition comprising at least one unique extract obtained from at least *Lycium barbarum* and at least one other plant, for example *Piper* and/or *Olea* europeae, and an extract of *Chrysanthellum indicum* and an extract of *Cynara scolymus*.

The unique extract from a mixture of plants "X" can be obtained using any suitable method, for example through a method comprising the following steps:
solid/liquid extraction
separation/pressing
filtration
evaporation
drying
optionally, incorporating additives
homogenization
packaging.

Preferably, one uses the whole plant or the exposed parts of *Chrysanthellum indicum* as plant raw material to obtain the unique extract. The unique extract is preferably made from at least 0.1% of the whole plant or exposed parts of *Chrysanthellum indicum* by weight relative to the total weight of the mixture of plants used to produce the unique extract.

Preferably, the leaves or roots of *Cynara scolymus* are used as plant raw material to obtain the unique extract. The unique extract is preferably made from at least 0.1% of the leaves or roots of *Cynara scolymus* by weight relative to the total weight of the mixture of plants used to produce the unique extract.

Preferably, the berries or exposed parts of *Lycium barbarum* are used as plant raw material to obtain the unique extract. The unique extract is preferably made from at least 0.1% of the berries or exposed parts of *Lycium barbarum* by weight relative to the total weight of the mixture of plants used to produce the unique extract.

Preferably, the unique extract comprises:
molecule(s) from *Chrysanthellum indicum* chosen from among apigenin-7-O-glucuronide, chrysanthellin A, chrysanthellin B, caffeic acid, luteolin, maritimetin, eriodictyol, isookanin, apigenin, luteolin-7-O-glucoside, maritimein, marein, eriodictyol-7-O-glucoside, flavomarein, apigenin-8-C-α-L-arabinoside-6-C-β-D-glucoside (shaftoside), apigenin-6,8-C-di-β-D-glucopyranoside (vicenin-2), or their analogues, and/or
molecule(s) from *Cynara scolymus* chosen from among a dicafeoylquinic acid, a sulfo-monocafeoylquinic acid, luteolin, luteolin-7-O-glucoside, luteolin-7-O-glucuronide, apigenin-7-O-glucoside, cynaropicrin, or analogues thereof, and/or
molecule(s) from *Lycium barbarum*, chosen from among polysaccharides such as xylose, mannose, arabinose or galactose.

The unique extract according to the invention preferably also comprises piperine, i.e., the unique extract is preferably also obtained from *Piper* or the composition may comprise piperine or an extract of *Piper* if the mixture of plants of the unique extract is not obtained from *Piper*. If the unique extract is obtained from a mixture of plants comprising *Piper*, one preferably uses the fruits or leaves of *Piper nigrum*, *Piper aduncum* and/or *Piper longum* as plant raw material to obtain the unique extract. The unique extract is preferably made from at least 0.0001% of the fruits or leaves of *Piper nigrum*, and/or *Piper aduncum* and/or *Piper longum* by weight relative to the total weight of the mixture of plants used to produce the unique extract.

The unique extract according to the invention can also be obtained from *Olea europaea* or the composition may comprise an extract of *Olea europaea* if the mixture of plants of the unique extract is not obtained from *Olea europaea*. If the unique extract is obtained from a mixture of plants comprising *Olea europaea*, one preferably uses the leaves or fruits of *Olea europaea* as plant raw material to obtain the unique extract. The unique extract is preferably made from at least 0.1% of the fruits of *Olea europaea* by weight relative to the total weight of the mixture of plants used to produce the unique extract.

If the unique extract is also obtained from *Olea europaea*, the unique extract preferably comprises oleuropein and/or hydroxytyrosol and/or their analogues.

Particularly suitable compositions according to the invention are in particular:
compositions comprising at least:
a unique extract obtained from *Chrysanthellum indicum, Cynara scolymus* and *Lycium barbarum*, and optionally from *Piper* and/or optionally from *Olea europaea*,
and optionally an extract of *Piper* and/or piperine and/or an extract of *Olea europeae;*
compositions comprising at least:
a unique extract obtained from at least *Chrysanthellum indicum* and *Cynara scolymus*, and optionally from *Piper* and/or optionally from *Olea europaea*,
an extract of *Lycium barbarum*,
and optionally an extract of *Piper* and/or piperine and/or an extract of *Olea europeae*,
compositions comprising at least:
a unique extract obtained from at least *Chrysanthellum indicum* and *Lycium barbarum*, and optionally from *Piper* and/or optionally from *Olea europaea*,
an extract of *Cynara scolymus*,
and optionally an extract of *Piper* and/or piperine and/or an extract of *Olea* europeae,
compositions comprising at least:
a unique extract obtained from at least *Cynara scolymus* and *Lycium barbarum*, and optionally from *Piper* and/or optionally from *Olea europaea*,
an extract of *Chrysanthellum indicum*,
and optionally an extract of *Piper* and/or piperine and/or an extract of *Olea europeae*,
compositions comprising at least:
a unique extract obtained from at least *Chrysanthellum indicum* and *Piper* and/or *Olea europeae*,
an extract of *Cynara scolymus* and an extract of *Lycium barbarum*,
and optionally an extract of *Piper* and/or piperine and/or an extract of *Olea europeae*,
compositions comprising at least:
a unique extract obtained from at least *Cynara scolymus* and *Piper* and/or *Olea europeae*,
an extract of *Chrysanthellum indicum* and an extract of *Lycium barbarum*,
and optionally an extract of *Piper* and/or piperine and/or an extract of *Olea europeae*,
compositions comprising at least:
a unique extract obtained from at least *Lycium barbarum* and *Piper* and/or *Olea europeae*,
an extract of *Chrysanthellum indicum* and an extract of *Cynara scolymus*,
and optionally an extract of *Piper* and/or piperine and/or an extract of *Olea europeae*.

The composition according to the invention comprising a unique extract, when it is intended for Humans, preferably comprises a quantity of unique extract corresponding to an administration of at least 0.00001 g, in particular between 0.00001 g and 0.60 g, of unique extract per kg of body weight of the person to whom the composition is administered and per day.

The compositions according to the invention in their various alternatives may be exclusively made up of the described elements (plant extracts and/or unique extract(s)), or may also comprise at least one additional element (products, molecules, extracts, active ingredients, excipients, etc.) added in addition to the plant extracts and/or the unique extract(s), said additional element preferably being able to be chosen from among:

the following vitamins: B1, B2, B3, B5, B6, B8, B9, B12 C, A, D, E, K1 and K2;
the following compounds: obeticholic acid, corosolic acid, polyunsaturated fatty acids in the Omega 6 and/or Omega 3 family, orotic acid, pangamic acid, para-amino-benzoic acid, amygdalin, beta-glucanes, carnitine, dimethylglycine, imeglimin, isoflavones, L-arginine, oxytocin, pectin, pyridoxamine, resveratrol, viniferine, L-citrulline;
the following oligo-elements and minerals: arsenic, boron, calcium, copper, iron, fluorine, iodine, lithium, manganese, magnesium, molybdenum, nickel, phosphorus, selenium, vanadium, zinc;
the following are nonessential micro-components: conjugated linolenic acid lipoic add, carotenoids, carnitine, choline, Q10 coenzyme, phytosterols, polyphonols in the tannin and lignan family, taurine;
fructo-oligosaccharides, galacto-oligosaccharides;
lactic ferments;
yeasts, for example red rice yeast (*Monascus purpureus*);
fungi, for example maitake;
products derived from insects compatible with the food and pharmaceutical sector;
marijuana and hashish;
coating agents: for example, hypromellose, microcrystalline cellulose, stearic acid, talc, sugar, shellac, povidone, beeswax;
aromas: for example, natural blueberry aroma or natural strawberry aroma;
acidifiers such as malic acid;
anti-caking agents: for example, silicon dioxide or magnesium stearate;
thickeners such as xanthan gum, colloidal silica, fatty acid mono and diglycerides;
stabilizers, such as calcium phosphate;
emulsifiers, such as soy lectin;
filler agents, such as cornstarch;
excipients: for example, microcrystalline cellulose, magnesium stearate or dicalcium phosphate.

The compositions according to the invention can also comprise one or several extracts of at least one of the following plant raw materials and/or one of the molecules contained in at least one of the following plant raw materials and/or the unique extract may also be obtained from at least one of the following plant raw materials: *Abelmoschus esculentus, Abies Alba, Abies balsamea, Abies sibirica, Acacia nilotica, Acacia senegal, Achillea millefollium, Achyranthes bidentata, Acmella oleracea, Actaea racemosa, Actinidia chinensis, Actinidia deliciosa, Adansonia digitata, Adianturn capillus-veneris, Aesculus hippocastanum, Afromomum melegueta, Agathosma betulina, Agathosma crenulata, Agathosma serratifolia, Agrimonia eupatoria, Ajuga reptans, Albizia julibrissin, Alchemilla vulgaris, Alliara petiolata, Allium ampeloprasum, Allium cepa, Allium sativum, Allium schoenoprasum, Allium ursinurn, Alnus glutinosa, Aloe ferox, Aloe vera, Aloysia citriodora, Alpinia galanga, Alpinia hainanensis, Alpinia officinarum, Alpinia oxyphylia, Althaea officinalis, Ammi visnaga, Amorphophallus konjac, Ananas comosus, Andographis paniculata, Anemarrhena asphodeloides, Anethum graveolens, Angelica archangelica, Angelica dahurica, Angelica pubescens, Angelica sinensis, Antennaria diocia, Anthriscus cerefolium, Anthyllis vuineraria, Aphanizomenon flos-aquae Ralfs, Apium graveolens, Arachis hypogaea, Aralia elata, Arctium lappa, Arctium minus, Argania spinosa, Armorica rustanica, Artemisia dracunculus, Artemesia vulgaris, Ascophyllum nodosum, Aspalathus linearis, Asparagus officinalis,*

*Astragalus membranaceus, Atractylodes lancea, Atractylodes macrocephala, Auracaria columnaris, Avena staiva, Ayahuasca, Baccharis genistelloides, Bacopa monnierri, Ballota nigra, Bambusa bambos, Bellis perennis, Berberis vulgaris, Beta vulgaris, Betula alleghaniensis, Betula pendula, Betula pubescens, Bixa orellana, Borago officnalis, Boswellia serrata, Brassica napus, Brassica nigra, Brassica oleracea, Brassica rapa, Bupleurum chinense, Calendula officinalis, Calluna vulgaris, Camellia sinsensis, Capsella bursa-pastoris, Capsicum annuum, Carex arenaria, Carica papaya, Carlina acaulis, Carphephorus odoratissmus, Carpinus betulus, Carthamus tinctorius, Carum carvi, Cassia fistula, Castanea sativa, Centaurea centaurium, Centaurea cyanus, Centaurium erythraea, Centella asiatica, Cerasus vulgaris, Ceratonia silliqua, Chaenomelum nobile, Chlorella vulgaris, Chondrus crispus, Chrysanthellum indicum, Cichorium intybus, Cinchona officinalis, cinchona pubescens, Cinnamomum camphora, Cinnamomum cassia, Cinnamomum verum, Cistanche salsa, Citrus incanus, Citrus aurantium, Citrus limon, Citrus maxima, Citrus medico, Citrus myrtifolia, Citrus reticulata blanco, Citrus sinsensis, Citrus paradisi, Clinopodium vulgare, Cnicus benedictus, Cochlearia officinalis, Cocos nucifera, Codonopsis pilosula, Coffea canephora, Coix lacryma-jobi* var. *mayyuen* Stapf; *Cola acuminata, Cola ballayi cornu, Cola nitida, Combretum micranthurn, Commiphora mukul, Conyza canadensis, Coriandrum sativum, Cornus officinalis, Corylus avellana, Corymbia citriodora, Crataegus laevigata, Craetegus monogyna, Crithmum maritimum, Crocus sativus, Cucumis meld, Cucurbita pepo, Cuminurn cyminum, Cupressus sempervirens, Cuscuta chinensis, Cyamopsis tetragonoloba, Cyathula officinalis, Cyclanthera pedata, Cydonia obionga, Cymbopogon martini, Cymbopogon nardus, Cymbopogon winterianus, Cynara cardunculus, Cyperus rotundus, Daucus carota, Dendranthema grandiflorum, Desmodium adscendens, Dimocarpus longan, Dioscorea oppostifolia, Dioscorea villosa, Diospyros kaki* Thunb., *Dunaliella saliena, Echinacea augustifolia, Echinacea pallida, Echinacea purpurea, Elaegnus rhamnoides, Alettaria cardamomum, Eleutherococcus senticosus, Elymus repens, Epiobium augustifolium, Epilobium parviflorum, Equisetum arvense, Erica cinerea, Erica tetralix, Eriobotrya japonica, Eriodictyon californicum, Erodium cicutarium, Eryngium campestre, Eschscholzia californica, Eucalyptus dives Schauer, Eucalyptus globulus, Eucalyptus radiata, Eucalyptus smithii* F. Muell, *Eucommia ulmoides, Eugenia uniflora, Eugenia jambolana, Euphrasia stricta* D. Wolff, *Euterpe oleracea, Fagopyrum esculentum* Moench, *Follopia japonica, Ferula assa-foetida, Ficus carica, Filipendula ulmaria, Foeniculum vulgare* Mill., *Forsythia suspensa, Fragaria dodonei* Ard., *Frangula purshiana* Cooper, *Fraxinus excelsior, Fraxinus ortus, Fucus serratus, Fucus vesiculosus, Fumaria officinalis, Galeopsis segetum* Neck., *Galium odotarum, Galium verum, Gardenia jasminoides* J. Ellis, *Gastrodia elata* Blume, *Gelidium corneum* J.V. Lamouroux, *Gentiana lutea, Geranium robertianum, Geum urbanum, Ginkgo biloba, Glycine max, Glycyrrhiza glabra, Glycyrrhiza uralensis, Gracilaria gracilis, Grindelia camporum* Greene, *Grindelia robusta* Nutt., *Grindelia squarrose* Dunal, *Gymnema sylvestris, Haematococcus pluvialis, Hamamemis virginiana, Harpagophytum procumbens, Harpagophytum zeyheri* Decne., *Hedeoma pluegioides* Pers., *Helianthus annuus, Helienthus tuberosus, Helichrysum arenarium, Helichrysum stoechas, Herniara glabra, Hibiscus sabdariffa, Hieracium pilosella, Himanthalia elongata, Hordeum vulgare, Houttuynia cordata* Thunb., *Huperzia serrata, Hyssopus officinalis, Ilex paraguariensis* A. St.-Hill, *Illicum verum, Impatients balsamina, Inula Britannica, Inula helenium, Jasminum grandiflorum, Jasmium officinale, Juniperus communis, Justicia adhatoda, Kavalama ureas, Krameria lappacea, Lagerstroemia speciosa, Laminaria digitata, Laminaria hyperborea, Lamium album, Larix decidua, Larix occidentalis, Laurus nobilis, Lavandula augustofolia, Lavandula latifoiia, Ledum palustre, Leonurus cardiaca, Lepidium meyenii* Walp., *Lepidium sativum, Lespedeza capitata, Levisticum officinale, Lindera aggregate, Linus usitatissimum, Liquidambar styraciflua, Lotus corniculatus, Lycium chinense, Lycopersicon esculentum, Lycopodium clavatum, Lycopus europaeus, Lythrum salicaria, Macadamia ternifolia* F. muell, *Macrocystis pyrifera, Magnolia officinalis, Malpighia glabra, Malus pumila, Malus domestics, Malus sylvestris, Malva sylvestris, Mangifera indica, Maranta arundinacea, Marrubium vulgare, Marsdenia cundurango, Marsdenia sylvestris, Mastocarpus stellatus, Matricaria chamomilla, Medicago sativa, Melaleuca alternifolia, Melaleuca cajuputi* Powell, *Melaleuca leucadendra, Melaleuca quinquenrvia, Melaleuca viridiflora, Melilotus altissimus* Thuill., *Melilotus officinalis, Mentha arvensis, Mentha* x *piperita, Menyanthes trifoliata, Mesembryanthemum crystallinum, Monarda didyma, Morinda citrifolia, Morinda officinalis, Morus alba, Morus nigra, Murraya koenigii, Musa* x *paradisiaca, Myrciaria dubia, Myristica flafgrans* Houtt., *Myroxylon balsamum, Myrtus communis, Nardostachys jatamansi, Nasturtium officinale* R. Br., *Nelumbo nucifera* Gaertn., *Nepeta cataria, Nepeta tenuifolia* Benth., *Nigella sativa, Ocimurn basilicum, Oenothera biennis, Ononis spinosa, Ophiopogon japonicus, Opuntia ficus-indica, Origanum compactum* Benth., *Origanum majorana, Origanum vulgare, Orthosiphon aristatus, Oryza sativa, Paeonia lactiflora, Paeonia* x *suffruticosa* Andrews, *Palmaria palmata, Panax ginseng, Panax quinquefolius, Panicum miliacium, Papaver rhoeas, Parietaria officinalis, Passiflora edulis* Sims, *Pastinaca sativa, Paullinia cupana* Kunth, *Pelargonium graveolens, Perilla frutescens, Persea americana, Persicaria bistorta, Persicaria maculosa* Gray, *Petroselinum crispum, Peucadanum ostruthium, Peumus boldus* Molina, *Phaseolus vulgaris, Phellodendron amurense, Photinia melancarpa, Phyllanthus emblica, Physalis alkekengi, Phymatolithon calcareum, Picea abies, Pimento dioca, Pimento racemosa, Pimpinella anisum, Pimpinella major, Pimpinella saxfraga, Pinus mugo* Turra, *Pinus pinaster* Alton, *Pinus sylvestris, Pistacia lentiscus, Plantago arenaria, Plantago lanceolata, Plantago major, Plantago ovata, Platycodon grandiflorus, Plectranthus barbatus* Andrews, *Pogostemom cablin, Polygala senega, Polygala sibirica, Polygala tenuifolia* Willd., *Polygonum aviculare, Populus nigra, Populus tremula, Populus tremuloides, Porphyra umbilicalis, Portulaca oleracea, Potentilla erecta, Primula veris, Prunella vulgaris, Prunus africana, Prunus armeniaca, Ribes nigrum, Ribes uva-crispa, Rosa canina, Rosa gallica, Rosa moschata, Rosa rubiginosa, Rosmarinus officinalis, Rubus caesius, Rubus fruticosus, Rubus idaeus, Rumex actetosa, Rumex acetosella, Rurnex crispus, Rumex patienta, Ruscus aculeates, Sachharina japonica, Saccharine, latissima, Salix alba, Salix fragilis, Salix pentandra, Salix purpurea, Salvia officinalis* L., *Salvia officinalis* subsp. *lavandulifolia* Gams, *Salvia sclarea, Sambucus nigra, Sanguisorba officinalis, Sanicula elata* Buch.-Ham. Ex D. Don, *Santalum album, Santolina chamaecyparissus, Saposhnikovia divaricata, Sargassum fusiforme, Satureja hortensis, Satureja montana, Saussurea costus, Scrophularia ningpoensis* Helmsl., *Scutellaria baicalensis* Georgi, *Secale cereale, Sedum acre, Sedum roseum, Senna alexandrina* Mill., *Senna obustifolia, Smilax cordifolia* Humb. & Bonpl.,

*Smilax glabra* Roxb., *Smilax officinalis* Kunth, *Smilax purhampuy* Ruiz, *Smilax purhampuy* Ruiz, *Smilax regelli* Killip and C.V. Morton, *Smilax vanillidora* Apt, *Solanum melongena, Solanum tuberosum, Solidago virgaurea, Sorbus aucuparia, Spatholobus suberctus* Dunn., *Spinacia oleracea, Spirulina major* Kützing, *Spirulina maxima* Geitler, *Spirulina platensis* Geitler, *Stavhys officinalis, Stemmacantha carthamoides* Dittrich, *Stypholobium japonicum, Syzgium aromaticum, Tagetes erecta, Tamarindus indica, Tanacetum parthemium, Terminalia* chebula Retz., *Theobroma cacao, Thymus saturejoides* Coss., *Thymus serpyllum, Thymus vulgaris, Thymus zygis, Tilia cordata* Mill., *Tilia platyphyllos* Scop., *Tilia tomentosa* Moench, *Tilia euopaea, Tribulus terrestris, Trichosanthes kirilowii* Maxim., *Trifolium arvense, Trifolium campestre* Schreb., *Trifolium pratense, Trifolium repens, Trigonella caerulea, Trigonella foenum-graecum, Tricitum aestivum, Tricitum durum* Desf., *Tricitum spelta* L., *Tricitum turgidum, Tropaeolum majus, Turnera diffusa Ulmus glabra* Huds., *Ulmus glabra* Huds., *Ulmus pumila, Ulmus rubra* Muhl., *Ulva lactuca, Uncaria gambir* Roxb., *Uncaria rhynchophylla* Miq., *Uncaria tomentosa* DC., *Undaria pinnatifida* Suringar, *Urtica dioca, Urtica urens, Vaccinium macrocarpon, Vaccinium oxyccocos, Vaccinium vitis-idae, Valeriana jatamansi* Jones, *Valeriana officinalis, Vanilla planifolia* Jacks, *Verbascum densiflorum* Bertol., *Verbascum thapsus, Verbena officinalis, Veronica officinalis, Viburnum opulus, Vigna angularis* Ohwi & H. Ohashi, *Vinca major, Vinca minor, Viola palustris, Viola tricolor, Vitex agnus-castus, Vitex trifolia, Vitis vinifera, Zea mays, Zingiber officinale* Roscoe, *Ziziphus jujuba* Mill.

The composition according to the invention may also optionally comprise an extract of *Vaccinum myrtillus*; the unique extract may be obtained from *Vaccinum myrtillus*.

The compositions according to the invention may also assume all forms, in particular the form of a powder, gel, emulsion or liquid, in particular in the form of tablets, capsules, gel caps, sticks, pouches, blisters, droppers or injectable form.

The compositions according to the invention may be used as nutritional products or health products, in particular as a medicament.

Nutritional products refer to all products have a nutritional and/or physiological effect, in particular including food supplements, foods, diet products, etc. These products can in particular be administered using the oral, gastric or venous route.

A health product in particular refers to all products having a beneficial effect on health, as prevention or treatment, whether this effect is physiological or pharmacological, in particular medicaments, pharmaceutical products. These products can in particular be administered using the oral, gastric, venous or cutaneous route.

The compositions according to the invention can be used to prevent and/or combat (or treat) fat and/or carbohydrate metabolism disorders in Humans or animals. *Chrysanthellum indicum, Cynara scolymus* and *Lycium barbarum* act synergistically, and this effect can be improved by the presence of piperine and/or *Olea europaea*.

In particular, the compositions according to the invention can be used to prevent and/or combat (or treat) dyslipidemia. They make it possible to decrease the total cholesterol level, the LDL cholesterol level, the circulating triglycerides and the hepatic triglycerides. They further have a HMG-CoA reductase inhibiting activity.

For such uses, the compositions according to the invention can be used in combination with a lipopenic therapeutic agent chosen from among:
 statins, in particular: simvastatin, pravastatin, fluvastatin, atorvastatin and rosuvastatin;
 statins associated with fixed doses, in particular: simvastatin+ezetimibe, pravastatin+acetylsalicilic acid, atorvastatin+amlodipine;
 fibrates, in particular: fenofibrate, bezafibrate, gemfibrozil, cipofibrate; nicotinic acid;
 ion exchange resins, in particular cholestyramine;
 cholesterol absorption inhibitors, in particular ezetimibe;
 omega-3 polyunsaturated fatty acids;
 tiadenol;
 agonists of the FXR (Farnesoid X Receptor) nuclear receptor.

The compositions according to the invention may also be used specifically to prevent or combat (or treat) obesity and excess weight and/or metabolic syndrome and/or pathological blood-pressure problems.

The compositions according to the invention can also be used to act on other cardiovascular or metabolic syndrome risk factors.

They are particularly suitable for preventing and/or combating type 2 diabetes in Humans or animals. Indeed, they make it possible to prevent the onset of chronic hyperglycemia, decrease the fasting blood glucose and glycated hemoglobin, circulating and hepatic triglycerides, body size and body fat mass, and to improve the tolerance for ingested carbohydrates and insulin sensitivity. They can be used as preventive treatment for type 2 diabetes and as first-line treatment, upon beginning hygiene-dietary measures, thereby making it possible to postpone the beginning of the standard oral antidiabetic molecules. They are also particularly suitable for the treatment of type 2 diabetes and its complications, nonalcoholic steatohepatitis (NASH) in particular, alone or in combination with other pharmacological treatments.

The compositions according to the invention may also be used in the prevention and/or treatment of type 1 diabetes and/or nonalcoholic fatty liver diseases, in particular nonalcoholic steatohepatitis (NASH), and/or cardiovascular pathologies, in particular coronary cardiopathies, cerebrovascular diseases, peripheral arteriopathies, deep vein thromboses, and/or pathologies related to insulin resistance, for example Alzheimer's disease (Bedse G et al. Front Neurosci 2015; 9:204).

For such uses, the compositions according to the invention may be used in combination with at least one antidiabetic therapeutic agent chosen from among biguanides, including metformin, dipeptidyl peptidase-IV (DPP-IV) inhibitors, analogues of glucagon-like peptide-1 (GLP-1), thiazolidinediones (TZDs), sulfonylureas, glycosidase inhibitors (acarbose, miglitol, voglibose, peptides containing the alanine-proline or proline-alanine sequence), fast and slow insulins, glycosidase inhibitors (acarbose, miglitol, voglibose), sodium-glucose co-transporter-2 (SGLT2) inhibitors, molecules in the fibranor family such as elafibranor, for molecules targeting nuclear receptors, and in particular the RORs (α, β, γ) and Rev-Erbs (α, β) receptors. The invention is now illustrated through examples of extract and compositions, and trial results demonstrating the efficacy of the compositions according to the invention, these examples and trials not being limiting.

I. EXAMPLES

Example 1: Dry Extract of *Chrysanthellum indicum*

The whole plant, fresh or dried, undergoes mechanical grinding until a coarse powder is obtained. This powder next undergoes a maceration step for 10 to 24 hours at ambient temperature in a 70/10 water/ethanol mixture, then the obtained assembly undergoes continuous lixiviation at 50° C. in a percolator with a 70/10 water/ethanol mixture, the plant/extract ratio being 3/1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a beige powder soluble in a water/alcohol mixture. This powder (dry extract) may be used directly or mixed in an appropriate solvent before use.

Example 2: Example of Dry Extract of *Cynara scolymus*

Artichoke in powdered form obtained from *Cynara scolymus* leaves undergoes a maceration step for 10 to 24 hours at ambient temperature in water, then the obtained assembly undergoes continuous lixiviation at 50° C. in a percolator with water, the plant/extract ratio being 2/1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a beige powder soluble in water.

Example 3: Example of Dry Extract of *Lycium barbarum*

Goji in powdered form obtained from *Lycium barbarum* leaves undergoes a maceration step for 10 to 24 hours at ambient temperature in water, then the obtained assembly undergoes continuous lixiviation at 50° C. in a percolator with water, the plant/extract ratio being 8/1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a beige to brown powder soluble in water.

Example 4: Example of Dry Extract of *Olea europaea*

Whole and air-dried olive tree leaves are ground at −80° C. using a cutting mill to obtain a fine and homogenous powder. The obtained powder next undergoes a maceration step for 10 to 24 hours in a 70/30 water/ethanol mixture. The step is carried out in a closed system with nitrogen bubbling at ambient temperature, or under a first microwave power of 800 W or under an ultrasound frequency of 20 kHz for 2×3 min. The obtained assembly then undergoes continuous lixiviation at SOT in a percolator with a 70/30 water/ethanol mixture, the plant/extract ratio being 10/1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a green powder in a water/alcohol mixture.

Example 5: Examples of Unique Extract of *Chrysanthellum indicum* and *Cynara scolymus*

Chrysanthellum in powdered form obtained from the exposed parts of *Chrysanthellum indicum*, and artichoke in powdered form obtained from the leaves of *Cynara scolymus*, undergo a maceration step for 10 to 24 hours at ambient temperature in water, then the obtained assembly undergoes continuous lixiviation at 50° C. in a percolator with water, the plants/unique extract ratio being 8 to 1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a beige powder soluble in water.

Example 6: Examples of Unique Extract of *Chrysanthellum indicum*, *Cynara Scolymus* and *Olea europaea*

Chrysanthellum in powdered form obtained from the exposed parts of *Chrysanthellum indicum*, and artichoke in powdered form obtained from the leaves of *Cynara scolymus* and olive tree in powdered form obtained from *Olea europaea* leaves, undergo a maceration step for 10 to 24 hours at ambient temperature in water, then the obtained assembly undergoes continuous lixiviation at 50° C. in a percolator with water, the plants/unique extract ratio being 4 to 1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a beige-brown powder soluble in water.

Example 7: Examples of Unique of *Chrysanthellum indicum*, *Cynara Scolymus* and *Lycium barbarum*

Chrysanthellum in powdered form obtained from the exposed parts of *Chrysanthellum indicum*, and artichoke in powdered form obtained from the leaves of *Cynara scolymus* and goji in powdered form obtained from *Lycium barbarum* berries, undergo a maceration step for 10 to 24 hours at ambient temperature in water, then the obtained assembly undergoes continuous lixiviation at 50° C. in a percolator with water, the plants/unique extract ratio being 4 to 1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a green-brown powder soluble in water.

Example 8: Examples of Unique Extract of *Chrysanthellum indicum*, *Cynara Scolymus*, *Lycium barbarum* and *Olea europaea*

The exposed parts of *Chrysanthellum indicum*, the leaves of *Cynara scolymus*, the berries of *Lycium barbarum* and the air-dried leaves of *Olea europaea* are ground at −−80° C. using a cutting mill to obtain a fine and homogenous powder. The obtained powder next undergoes a maceration step for 10 to 24 hours in a 70/30 water/ethanol mixture. The step is carried out in a closed system with nitrogen bubbling at ambient temperature, or under a first microwave power of 800 W or under an ultrasound frequency of 20 kHz for 2×3 min. The obtained assembly then undergoes continuous lixiviation at 50° C. in a percolator with a 60/40 water/ethanol mixture, the plant/extract ratio being 8/1. The obtained extract next undergoes liquid/liquid washes using a nonpolar organic solvent such as di- or tri-chloromethane. After concentration by low-pressure evaporation at 35° C., one obtains a liquid which, freeze-dried for 24 hours, yields a brown-beige powder in a water/alcohol mixture.

Example 9: Example of Composition According to the Invention in Powdered Form to be Reconstituted, Comprising Three Plant Extracts The composition of example 9 assumes the form of tablets able to be administered orally. They comprise, expressed in percentage by weight, relative to the total weight of the composition, 15.6% dry extract of the exposed parts of *Chrysanthellum americanum*, 15.6% dry extract of leaves of *Cynara scolymus*, and 23.5% dry extract of fruits of *Lycium barbarum*. The composition also comprises vitamins B1, B2, B3, PP, B5, B6, H, B9, B12 and D3, as well as zinc and chromium. As excipients, it comprises dicalcium phosphate and microcrystalline cellulose.

The composition for 1 tablet is indicated in the following table.

| List of ingredients | For 1 tablet |
| --- | --- |
| Dry extract of exposed parts of *Chrysanthellum indicum* | 125 mg |
| Dry extract of *Cynara scolymus* leaves | 125 mg |
| Dry extract of *Lycium barbarum* fruits | 187.5 mg |
| Vitamin B1 | 0.36 mg |
| Vitamin B2 | 0.45 mg |
| Vitamin PP | 5.3 mg |
| Vitamin B5 | 2 mg |
| Vitamin B6 | 0.46 mg |
| Vitamin H - Biotin | 16.6 µg |
| Vitamin B9 | 66 µg |
| Vitamin B12 | 0.83 µg |
| Vitamin D3 | 1.6 µg |
| Zinc | 3.3 mg |
| Chromium | 13 µg |
| Dicalcium phosphate | 198 mg |
| Microcrystalline cellulose | 153.44 mg |
| Total weight | 798 mg |

Example 10: Example Composition According to the Invention in the Form of Gel Caps, Comprising Four Plant Extracts The composition assumes the form of gel caps able to be administered orally. It comprises, expressed in percentage by weight, relative to the total weight of the composition, 16.6% dry extract of the whole plants of *Chrysanthellum americanum* and 16.6% dry extract of leaves of *Cynara scolymus*, 33.3% fruits of *Olea Europaea* and 25% fruits of *Lycium barbarum*. The composition also comprises a lactic ferment such as *Lactobacillus delbrueckii* ssp. *Bulgaricus*. As an emulsifier, it comprises soy lectin from the non-GMO channel, as thickeners, colloidal silica and fatty acid mono- and diglycerides.

The capsule is a fish gelatin, with glycerin and a dye, red iron oxide.

The composition of such a product is indicated in the following table.

| List of ingredients | For 1 gel cap |
| --- | --- |
| Dry extract of whole plants of *Chrysanthellum indicum* | 100 mg |
| Dry extract of *Cynara scolymus* leaves | 100 mg |
| Dry extract of *Olea europaea* fruits | 200 mg |
| Dry extract of *Lycium barbarum* fruits | 150 mg |
| *Lactobacillus delbrueckii* ssp. *Bulgaricus* | $10 \cdot 10^9$ CFU |
| Total weight | 600 mg |

CFU: Colony-Forming Unit.

Example 11: Example Composition According to the Invention in the Form of Gel Caps, Comprising a Unitary Extract of Three Plants The composition assumes the form of gel caps able to be administered orally. It comprises a unique hydroalcoholic extract of a powder mixture obtained from the exposed part of *Chrysanthellum americanum*, leaves of *Cynara scolymus*, and fruits of *Lycium barbarum*. The ratio between the three plants is 1/1/1.5. The unique extract of the mixture is obtained using a method comprising the following steps:
solid/liquid extraction
separation/pressing
filtration
evaporation
drying
optionally, incorporating additives
homogenization
packaging.

Example 12: Example Composition According to the Invention in the Form of Tablets, Comprising a Unitary Extract of Three Plants Plus a *Piper nigrum* Extract The composition assumes the form of tablets able to be administered orally. It comprises a unique hydroalcoholic extract of a powder mixture obtained from the exposed part of *Chrysanthellum americanum*, leaves of *Cynara scolymus*, and fruits of *Lycium barbarum*. The ratio between the three plants is 1/1/1.5. It also comprises a hydroalcoholic extract of *Piper nigrum* fruits containing piperine. Upon stabilizing, the composition may comprise bicalcium orthophosphate; as anti-caking agents, fatty acid magnesium salts, silicon dioxide and fatty acids; as coating agent, hydroxypropyl methyl cellulose; as dyes, Allura red AC and titanium oxide.

The composition of active ingredients for 1 tablet is indicated in the following table.

| List of ingredients | For 1 tablet |
| --- | --- |
| Dry extract of a mixture of exposed part of *Chrysanthellum americanum*, leaves of *Cynara scolymus*, and fruits of *Lycium barbarum* | 450 mg |
| Dry extract of *Piper nigrum* fruits | 3 mg |
| Total weight | 453 mg |

II. In Vivo Evaluation of the Efficacy of the Composition

In vivo experiments on mice have been conducted to demonstrate the effects of the compositions according to the invention, in particular on total cholesterol and LDL cholesterol, and also on the serous triglyceride level, insulin sensitivity and fasting blood glucose. The experiments were done on db/db mice. The db/db mice represent a mutation of the leptin receptors causing a disorder of the cellular signaling of the latter. The leptin receptors are highly expressed at the hypothalamus. The mice having a mutation of these receptors cannot effectively regulate their energy stores. This results in a high insulinemia as of the first days of life (10-14 days), and obesity from 3 to 4 weeks with an increased blood glucose. These mice are hypocholesterolemic, hypertriglyceridemic, insulin resistant and glucose intolerant. They further constitute a relevant and predictive model for one of the complications of type 2 diabetes, nonalcoholic steatohepatitis (NASH) (Aileen J F King Br J Pharmacol 2012; 166(3):877-894; Sanches S C et al. Biomed Res Int 2015).

II.a Chrysanthellum indicum, Cynara Scolymus Association

The experimental time was 9 weeks with a "Run-in" of 1 week followed by 8 weeks of supplementation with the plant extracts and a composition X. The male mice were 10 weeks old at the beginning of treatment.

3 compositions X were tested. These compositions were directly integrated into the food of the rodents, which makes it possible to ensure their "multi-target" efficacy and large-scale use, intravenous or intraperitoneal injections being limited to a small number of people, given their administration method. This also avoids daily gavage, which alters various physiological processes.

The tested compositions were the following:

C1: *Chrysanthellum indicum* (whole plant, 1% food);
C2: *Cynara scolymus* (leaves, 1% food);
C3: *Chrysanthellum indicum* (whole plant)+*Cynara scolymus* (leaves) (1% and 1% of the food, respectively).

The aforementioned plants were dry extracts obtained from plant raw materials.

The experimental assessments in particular pertained to:

The measurement of the serous lipids (total cholesterol, LDL cholesterol, triglycerides);

The evolution of the blood glucose during an oral sensitivity test to insulin. This test consisted of an intraperitoneal injection of insulin (2 U/kg) on an empty stomach. The evolution of the blood glucose in response to the insulin injection was measured in the tail by biopsy just before the injection (t0), then after 30, 60, 90 and 120 minutes. The area under the curve (AUC) was calculated. A decrease in the AUC reflects a better response to the insulin injection, and therefore improved insulin sensitivity. Conversely, an increase in the AUC reflects a lower quality sensitivity to the insulin, and therefore insulin resistance;

The measurement of the fasting blood glucose.

The evaluations presented were done just before the supplementation (t=0) and at the end of supplementation (t=8 weeks).

Total Cholesterol, LDL Cholesterol and Serous Triglycerides

The obtained results are shown in Table 1 below.

TABLE 1

Effect of the composition according to the invention on cholesterol

| Parameters | Control | C1 | C2 | C3 |
|---|---|---|---|---|
| Total serous cholesterol (mg/dL) | 198.4 ± 12.2 | 194.0 ± 9.2 | 162.9 ± 13.6 | 108.9 ± 6.6 [c] |
| Serious LDL cholesterol (mg/dL) | 118.2 ± 10.2 | 104.0 ± 5.6 | 85.1 ± 7.9 [b] | 58.0 ± 2.8 [c] |
| Serious triglycerides (mg/dL) | 262.2 ± 17.3 | 262.3 ± 19.6 | 191.5 ± 10.1 [b] | 181.1 ± 18.3 [b] |

Mean values ± SEM.
For total cholesterol measurements: Control = 11; C1 = 12; C2 = 13 and C3 = 14.
For serous LDL cholesterol measurements: Control = 11; C1 = 12; C2 = 12 and C3 = 14.
For serous triglyceride measurements: Control = 11; C1 = 12; C2 = 12 and C3 = 14.
Student t test for unpaired data,
[b] C2 versus Control,
[c] C3 versus Control, p < 0.05. No significant difference between the Control and C1 groups.

The results presented in Table 1 show a very significant effect of composition C3 according to the invention on the total cholesterol, LDL cholesterol and serous triglycerides. In the context of patients with mixed dyslipidemia (increased LDL cholesterol and triglycerides), the statin (to decrease the LDL cholesterol)+fibrates (to decrease the triglycerides) drug combination may prove dangerous. Indeed, the risk of myopathies is exacerbated with the simultaneous administration of statins and fibrates (Denke M A J Manag Care Pharm 2003; 9:17-9). However, it is essential to decrease the blood triglyceride level, since a high level increases the risk of atherosclerosis (Brinton E A Cardiol Clin 2015; 33:309-323). Statins may also increase the risk of other pathologies, such as breast cancer (from Lorgeril M et al. BMC Med 2014; 12:94). Composition C3 according to the invention therefore makes it possible to respond to a major health issue, since it makes it possible to decrease both the LDL cholesterol and serous triglycerides. Insulin Sensitivity Insulin resistance is one of the most important mechanisms of the development of many pathologies, including metabolic syndrome and atherosclerosis (Samuel V T et al. Cell 2012; 148:852-71+Kim B et al. Exp Mol Med 2015; 47(3):e149). Composition C3 according to the invention significantly improves the insulin sensitivity (results illustrated in FIG. 1). The effects on the circulating lipids and insulin sensitivity therefore make it an extremely interesting composition for the prevention and treatment of metabolic syndrome and atherosclerosis. Furthermore, the improved insulin sensitivity with composition C3 according to the invention is particularly interesting for the prevention and treatment of type 2 diabetes and its complications. Indeed, insulin resistance is one of the major mechanisms for the progression of type 2 diabetes (Samuel V T et al. Cell 2012; 148:852-71). Lastly, by acting on this parameter, composition C3 according to the invention is particularly suitable in the other pathologies for which one major cause is insulin resistance. This is in particular the case for one of the complications of type 2 diabetes, nonalcoholic steatohepatitis (NASH; Samuel V T et al. Cell 2012; 148:852-71), and Alzheimer's disease (Bedse G et al. Front Neurosci 2015; 9:204).

Fasting Blood Glucose

Composition C3 decreases the fasting blood glucose by 10% (control group, 537 mg/dL versus group C3, 488 mg/dL), whereas metformin, the reference therapeutic agent in the treatment of type 2 diabetes, increases the fasting blood glucose by 11% on the same model, but in an experiment where the mice were younger and consequently had a lower fasting blood glucose relative to the Control mice presented above (control group, 414 mg/dL versus metformin 463 mg/d L).

Synergistic Effect

Furthermore, the synergistic effect has been evaluated according to the Colby SR method described in "Calculation of the synergistic and antagonistic responses of herbicide combinations" Weeds, 1967, 15:20-22. This method was in particular used in patent EP03812880. For each combination, the synergy factor was calculated. A factor >1 indicates the existence of a synergistic effect. A factor <1 indicates the existence of an antagonist. The calculations performed are:

Expected efficacy rate=$A+B-(A*B/100)$

Synergy factor $(SF)$=(1*observed efficacy rate (%))/ expected efficacy rate (%)

The calculations pertained to the following combination:
Calculation of SF for composition C3 where A=C1 and B=C2
Table 2 below provides the results for the combination C1+C2=C3.

TABLE 2

Synergy factors for the combination C1 + C2 = C3

| | Observed efficacy rate (in % of the control group) | | | Efficacy rate | |
|---|---|---|---|---|---|
| | C1 Chrysanthellum indicum | C2 Cynara scolymus | C3 Chrysanthellum indicum + Cynara scolymus | expected with C3 | Synergy factor |
| Total cholesterol | −2.2% | −17.9% | −45.1% | −19.7% | 2.29 |
| LDL cholesterol | −12.0% | −28.0% | −50.9% | −36.6% | 1.39 |

Figure 2:
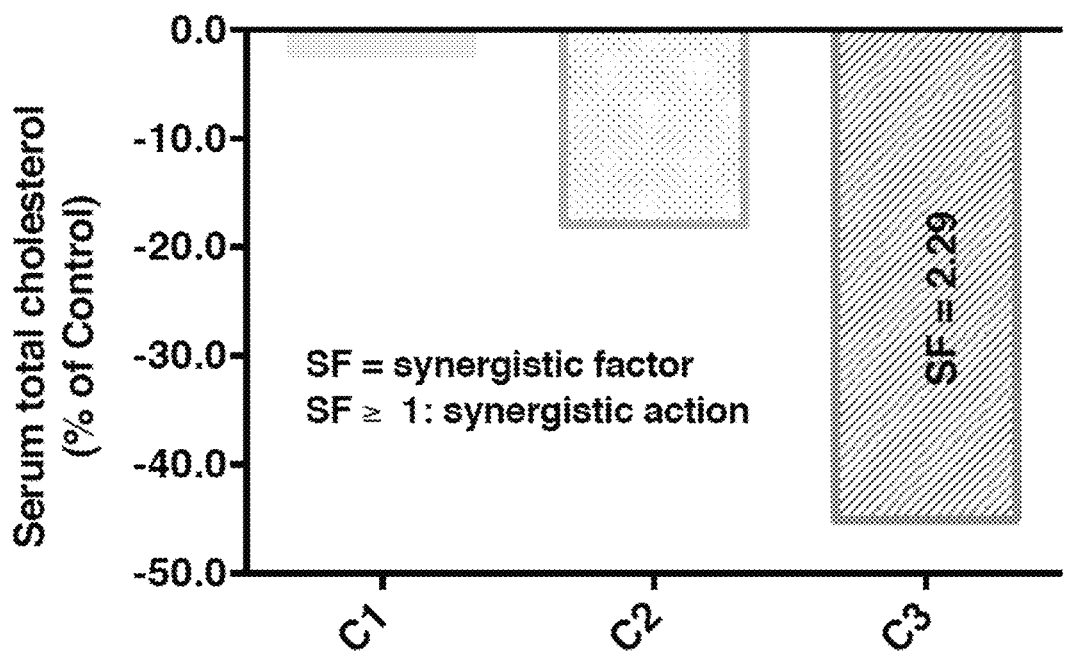
FIG. 2: the results demonstrating the synergistic effect provided by a composition comprising molecules extracted from *Chrysanthellum indicum* and *Cynara scolymus*, these results corresponding to the results of Table 2 for the total cholesterol (point II)
Figure 3:
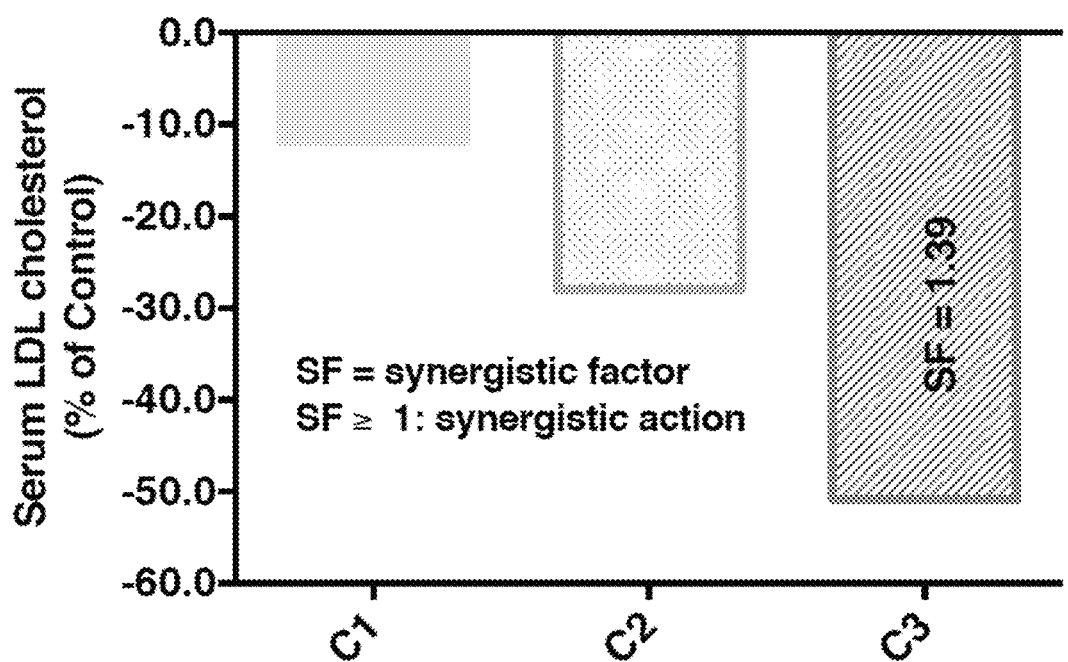
FIG. 3: the results demonstrating the synergistic effect provided by a composition comprising molecules extracted from *Chrysanthellum indicum* and *Cynara scolymus*, these results corresponding to the results of Table 2 for the LDL cholesterol (point II)

The combination of C1 and C2, i.e., C3, unambiguously demonstrates a very significant and surprising synergistic effect both on the total cholesterol level (FIG. 2) and the serous LDL cholesterol level (FIG. 3).

II.b Chrysanthellum indicum, Cynara scolymus, Lycium barbarum Association

The experimental time was 6 weeks with a "Run-in" of 1 week followed by 6 weeks of supplementation with the plant extracts and a composition X. The male mice were 6 weeks old at the beginning of treatment.

1 composition X was tested. This composition was directly integrated into the food of the rodents, which makes it possible to ensure their "multi-target" efficacy and large-scale use, intravenous or intraperitoneal injections being limited to a small number of people, given their administration method. This also avoids daily gavage, which alters various physiological processes.

The tested composition was the following:
C4: Chrysanthellum indicum (exposed parts)+Cynara scolymus (leaves)+Lycium barbarum (1%, 1% and 1% of the food, respectively).

The aforementioned plants were dry extracts obtained from plant raw materials.

The experimental evaluation pertained to the hepatic triglyceride levels at the end of supplementation (t=6 weeks). The obtained results are shown in Table 3 below.

TABLE 3

Effect of the composition according to the invention on hepatic triglyceride concentrations

| Parameters | Control | C4 |
|---|---|---|
| Concentration in liver (hepatic) triglycerid (µmol/mg of tissue) | 49.51 ± 5.39 | 17.36 ± 1.87 [a] |

Mean values ± SEM.
Control = 10; C4; n = 10.
Student t test for unpaired data,
[a] $p < 0.0001$.

Figure 4:
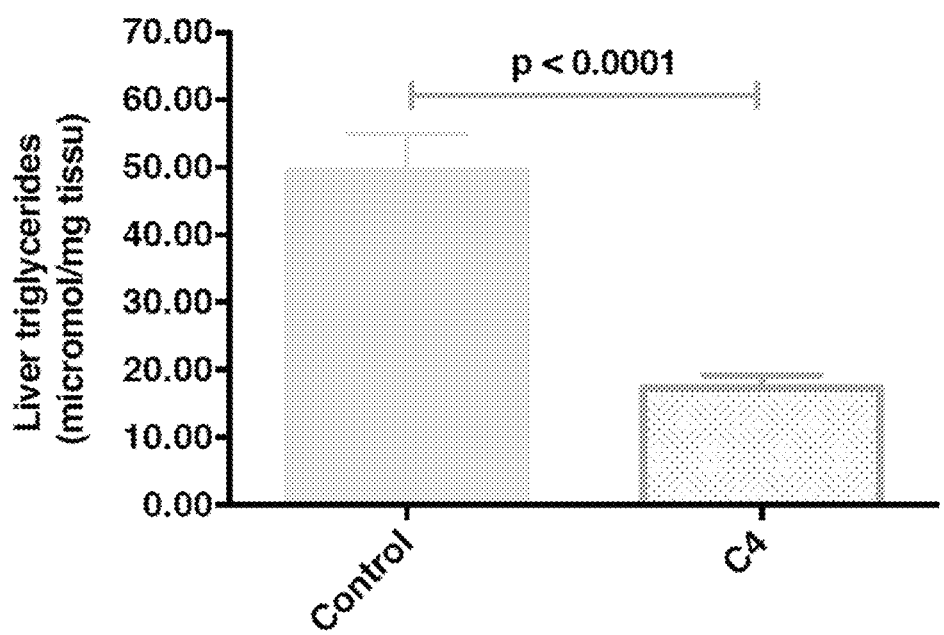
FIG. 4: the results demonstrating the effects of the association of *Chrysanthellum indicum*, *Cynara scolymus* and *Lycium barbarum* on hepatic triglycerides.

The results presented in Table 3 show a very significant effect of composition C4 according to the invention on the hepatic triglycerides. The results are also illustrated in FIG. 4.

What is claimed is:

1. A tablet, capsule, powder, gel, emulsion or liquid for lowering levels of low-density lipoprotein cholesterol and triglycerides in the blood of a human, consisting essentially of therapeutically effective amount of a mixture of a Chrysanthellum indicum extract, Cynara scolymus extract, a Lycium barbarum extract, and an extract selected from the group consisting of piperine, Piper extract, Olea europeae extract, Vaccinium myrtillus extract and any combination thereof, wherein the Chrysanthellum indicum extract, the Cynara scolymus extract and the Lycium barbarum extracts are in a ratio from 0.001:0.001:0.001 to 10:10:10, respectively.

2. A method of treating a pathological disorder in a human in need thereof wherein said pathological disorder is selected from the group consisting of dyslipidemia, type 1 diabetes, type 2 diabetes, a nonalcoholic fatty liver disease, nonalcoholic steatohepatitis, coronary cardiopathy, cerebrovascular disease, peripheral ateriopathy, deep vein thrombosis and any combination thereof, the method consisting essentailly of administering to the human or animal the tablet, capsule, powder, gel, emulsion or liquid of claim 1.

3. The method of claim 2, wherein the method further consists essentially of administering to the human or animal a therapeutic agent selected from the group consisting of a statin, a fibrate, nicontic acid, an ion exchange resin, a cholseterol absorption inhibitor, omega-3-polyunsaturated fatty acids, tiadenol, a Farnesoid X Receptor nuclear receptor agains and any combinations thereof.

4. The method of claim 2, wherein the method further consists essentially of administering to the human or animal at least one antidiabetic thereapeutic agent.

5. The method of claim 4, wherein the antidiabetic therapeutic agent is selected from the group consisting of metformin, a dipeptidyl peptidase-IV inhibitor, an analogue of glucagon-like peptide-1, thiazolidinediones, sulfonylureas, glycosidase inhibitors, acarbose, miglitol, voglibose, and any combinations thereof.

6. The method of claim 3, wherein the human is obese and/or has one or more of the following: excess weight, metabolic syndrome, Alzheimer's disease and/or pathological high-blood pressure.

7. A method for making the tablet, capsule, powder, gel, emulsion or liquid of claim 1, the method consisting essentially of:
- extracting each of *Chrysanthellum indicum, Cynara scolymus* and *Lycium barbarum* separately and then mixing the three extracts together to form a mixture of the three extracts; and
- mixing the mixture of the three extracts with an extract selected from the group consisting of *Pipe* extract and an *Olea europaea* extract to yield the tablet, capsule, powder, gel, emulsion or liquid of claim 1.

8. The tablet, capsule, powder, gel, emulsion or liquid of claim 1, wherein the tablet, capsule, powder, gel, emulsion or liquid consists essentially of the therapeutically effective amount of the mixture of the *Chrysanthellum indicum* extract, the *Cynara scolymus* extract, the *Lycium barbarum* extract, and the exttact consisting of *Olea europeae* extrtact and one or both from piperine and Piper extract.

* * * * *